United States Patent
Shankar

(10) Patent No.: US 10,806,628 B2
(45) Date of Patent: Oct. 20, 2020

(54) DUAL CAP SYSTEM FOR CONTAINER-CLOSURES TO MAINTAIN TIP STERILITY DURING SHELF STORAGE

(71) Applicant: ALLERGAN, INC., Irvine, CA (US)

(72) Inventor: Sai Shankar, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 1345 days.

(21) Appl. No.: 13/952,240

(22) Filed: Jul. 26, 2013

(65) Prior Publication Data

US 2014/0031767 A1    Jan. 30, 2014

Related U.S. Application Data

(60) Provisional application No. 61/675,909, filed on Jul. 26, 2012.

(51) Int. Cl.
*A61F 9/00* (2006.01)
*A61J 1/14* (2006.01)
(Continued)

(52) U.S. Cl.
CPC .......... *A61F 9/0008* (2013.01); *A61J 1/1475* (2013.01); *A61K 31/205* (2013.01);
(Continued)

(58) Field of Classification Search
CPC ..... A61F 9/0008; A61J 1/1475; A61J 1/2072; A61J 1/065; A61J 1/067; A61J 1/18; A61J 1/1418; A61J 1/2037; A61J 1/1425; A61K 31/205; A61K 31/407; A61K 31/496; A61K 31/498; A61K 31/5377; A61K 31/5575; A61K 31/573; A61K 38/13

See application file for complete search history.

(56) References Cited

U.S. PATENT DOCUMENTS

| 4,610,374 A | 9/1986 | Buehler |
| 5,074,440 A | 12/1991 | Clements et al. |

(Continued)

FOREIGN PATENT DOCUMENTS

| CA | 2492255 | 7/2006 |
| CN | 2428431 | 5/2001 |

(Continued)

OTHER PUBLICATIONS

Merriam Webster: sterile, https://web.archive.org/web/20111007130645/http://www.merriam-webster.com/dictionary/sterile, accessed Oct. 30, 2016, captured Oct. 7, 2011.*

(Continued)

*Primary Examiner* — Ariana Zimbouski
(74) *Attorney, Agent, or Firm* — Lorenz Siddiqi

(57) ABSTRACT

A container-closure system includes a container configured to hold a therapeutic liquid and having a dispensing tip configured to dispense a dose of the therapeutic liquid. A vented cap is configured to fit over at least a portion of the container including the dispensing tip and having one or more vents that allow air to pass into and out of a cavity defined between the vented cap and the dispensing tip. A second cap is configured to fit over at least a portion of the vented cap. A tamper evident seal is coupled to the second cap and one or both of the container and the vented cap.

20 Claims, 7 Drawing Sheets

(51) Int. Cl.
*A61K 38/13* (2006.01)
*A61K 31/5377* (2006.01)
*A61K 31/573* (2006.01)
*A61K 31/205* (2006.01)
*A61K 31/407* (2006.01)
*A61K 31/496* (2006.01)
*A61K 31/498* (2006.01)
*A61K 31/5575* (2006.01)
*A61J 1/18* (2006.01)
*A61J 1/06* (2006.01)
*A61J 1/20* (2006.01)

(52) U.S. Cl.
CPC .......... *A61K 31/407* (2013.01); *A61K 31/496* (2013.01); *A61K 31/498* (2013.01); *A61K 31/5377* (2013.01); *A61K 31/5575* (2013.01); *A61K 31/573* (2013.01); *A61K 38/13* (2013.01); *A61J 1/065* (2013.01); *A61J 1/067* (2013.01); *A61J 1/1425* (2015.05); *A61J 1/18* (2013.01); *A61J 1/2037* (2015.05); *A61J 1/2072* (2015.05)

(56) References Cited

U.S. PATENT DOCUMENTS

| | | | |
|---|---|---|---|
| 5,451,374 A * | 9/1995 | Molina | A61J 1/1475 215/248 |
| 5,718,346 A | 2/1998 | Weiler | |
| 5,921,444 A | 7/1999 | Fuchs | |
| 6,000,580 A | 12/1999 | Nilson | |
| 6,062,433 A | 5/2000 | Fuchs | |
| 8,006,870 B2 | 8/2011 | Stadelhofer et al. | |
| 8,292,129 B2 | 10/2012 | Stadelhofer et al. | |
| 8,561,859 B2 | 10/2013 | Wochele et al. | |
| 2005/0139611 A1 * | 6/2005 | Kubo | B65D 47/06 222/189.06 |
| 2006/0011654 A1 | 1/2006 | Webb | |
| 2010/0084436 A1 * | 4/2010 | Arvizu | B65D 75/5883 222/525 |
| 2010/0108712 A1 * | 5/2010 | Manesis | A61F 9/0008 222/1 |
| 2011/0127294 A1 * | 6/2011 | Pearcy | B01L 3/0272 422/501 |
| 2012/0279968 A1 * | 11/2012 | Levy Sarraf | B65D 47/265 220/288 |
| 2013/0020227 A1 * | 1/2013 | Stack | A61J 1/16 206/570 |
| 2013/0075431 A1 | 3/2013 | Wochele | |

FOREIGN PATENT DOCUMENTS

| | | |
|---|---|---|
| CN | 2781756 | 5/2006 |
| CN | 101018716 | 8/2007 |
| EP | 0611357 | 8/1996 |
| EP | 2152599 | 2/2012 |
| EP | 1495747 | 1/2013 |
| GB | 849578 | 9/1960 |
| KR | 88-0003522 | 10/1988 |
| KR | 2000394590000 | 1/1989 |
| WO | 9310015 | 5/1993 |
| WO | 9324164 | 12/1993 |
| WO | 2008110014 | 9/2008 |
| WO | 2008142721 | 11/2008 |
| WO | 2009000279 | 12/2008 |
| WO | 2012076626 | 6/2012 |
| WO | 2013075951 | 3/2013 |

OTHER PUBLICATIONS

International Searching Authority, Notification of Transmittal of the International Search Report and the Written Opinion of the International Searching Authority, PCT/US2013/052237, dated Nov. 8, 2013.

* cited by examiner

DUAL CAP SYSTEM FOR CONTAINER-CLOSURES TO MAINTAIN TIP STERILITY DURING SHELF STORAGE

RELATED APPLICATION

This application claims the benefit of U.S. Provisional application Ser. No. 61/675,909, filed Jul. 26, 2012, the disclosures of which are hereby incorporated in their entirety herein by reference.

SUMMARY

Embodiments of the disclosure are directed to container-closure systems and drug delivery systems that include a vented cap and an over cap. According to some embodiments, a container-closure system includes a container configured to hold a therapeutic liquid and having a dispensing tip configured to dispense a dose of the therapeutic liquid. A vented cap is configured to fit over at least a portion of the container including the dispensing tip and having one or more vents that allow air to pass into and out of a cavity defined between the vented cap and the dispensing tip. A second cap is configured to fit over at least a portion of the vented cap. A tamper evident seal is coupled to the second cap and one or both of the container and the vented cap.

According to various aspects, the container is configured to dispense a plurality of single doses of the therapeutic liquid in the form of an ophthalmic solution, emulsion or suspension. In some embodiments, the therapeutic agent is selected from the group consisting of bimatoprost, brimonidine, timolol, cyclosporine, gatifloxacin, ocufloxacin, prednisolone, carnitine and ketorolac. In some cases, one or more vents in the vented cap are configured to allow passage of air into and out of the cavity sufficient to accelerate drying of residual therapeutic liquid at the dispensing tip of the container after dispensing the therapeutic liquid dose.

In some cases, the second cap is configured to be twisted and removed from the apparatus, and the tamper evident seal is configured to break in response to the twisting of the second cap. According to various implementations, the vented cap and the second cap define an integral structure, and the tamper evident seal is configured to break away from the second cap. In accordance with some embodiments, the vented cap, the second cap, and the tamper evident seal define an integral structure, and the tamper evident seal is configured to break away from the vented cap and the second cap. According to some aspects, the second cap defines a second vented cap, and twisting the second vented cap relative to the container causes vents of the vented cap and the second vented cap to overlap.

According to some implementations, the vented cap comprises a protrusion arranged on the vented cap to establish contact with the dispensing tip of the container when the vented cap is fitted on the container. In some cases, the protrusion is configured to seal the dispensing tip of the container when the vented cap is fitted on the container.

According to various implementations, the second cap comprises a desiccant system. In some cases, one or both of the dispensing tip of the container and the vented cap comprise an antimicrobial. In accordance with various embodiments, the therapeutic liquid is a preservative-free therapeutic liquid. In some cases, the container comprises a uni-directional valve situated at the dispensing tip and configured to prevent fluid return into the container. According to some embodiments, the uni-directional valve is configured to prevent contamination of the therapeutic liquid from a source external to the container. In some cases, the container and the dispensing tip are formed of one or more polymers selected from the group consisting of low-density polyethylene, high-density polyethylene, and high-impact polystyrene.

According to further embodiments, a method involves storing a therapeutic liquid in a reservoir of a container configured to hold the therapeutic liquid. The container comprises a dispensing tip configured to dispense a dose of the therapeutic liquid. A vented cap is configured to fit over at least a portion of the container including the dispensing tip and having one or more vents that allow air to pass into and out of a cavity defined between the vented cap and the dispensing tip. A second cap is configured to fit over at least a portion of the vented cap. A tamper evident seal is coupled to the second cap and one or both of the container and the vented cap. In some embodiments, the container is configured to dispense a plurality of single doses of the therapeutic liquid in the form of an ophthalmic solution, emulsion or suspension.

According to further embodiments, a method involves removing a cap from a container configured a hold the therapeutic liquid, the container comprising a dispensing tip configured to dispense a dose of the therapeutic liquid. The cap comprises a vented cap configured to fit over at least a portion of the container including the dispensing tip and having one or more vents that allow air to pass into and out of a cavity defined between the vented cap and the dispensing tip. A second cap is configured to fit over at least a portion of the vented cap. The method further includes dispensing the therapeutic liquid from the container.

These and other features can be understood in view of the following detailed discussion and the accompanying drawings.

DISCLOSURE

Embodiments of the disclosure are generally directed to container-closure and drug delivery systems. According to some embodiments, the container-closure or drug delivery systems are configured for dispensing multiple single doses of a therapeutic agent in the form of a solution, emulsion or suspension through a dispensing tip. After administering a dose of the therapeutic agent, residual amounts of the agent and/or other contaminants, such as bodily fluids, may remain on the outside surface of the dispensing tip. The residual material that is left on the dispensing tip has the potential to promote microbial growth. Vents may be added to a cap of the container to accelerate drying time of the residual agent and thus reducing the potential for microbial growth. During storage of the container, the vents in the cap may decrease the sterility of the container by allowing ambient air to come into contact with the dispensing tip. An over cap is arranged over at least a portion of the vented cap, covering the vents on the vented cap and reducing the potential for the sterility of the dispensing tip being compromised.

Figure 1:
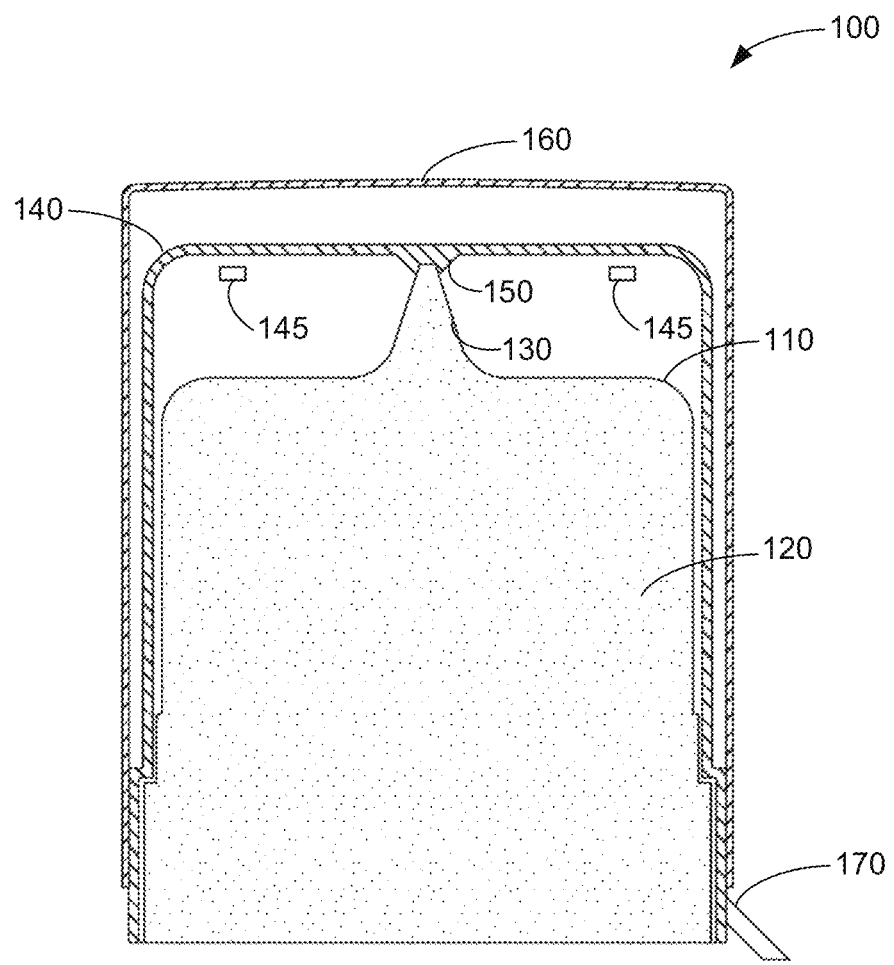
FIGS. 1 and 2 show a container-closure system that includes a vented cap, an over cap, and a tamper evident configured to be broken causing the tamper-evident seal and the over cap to be removed from the container.
Figure 2:
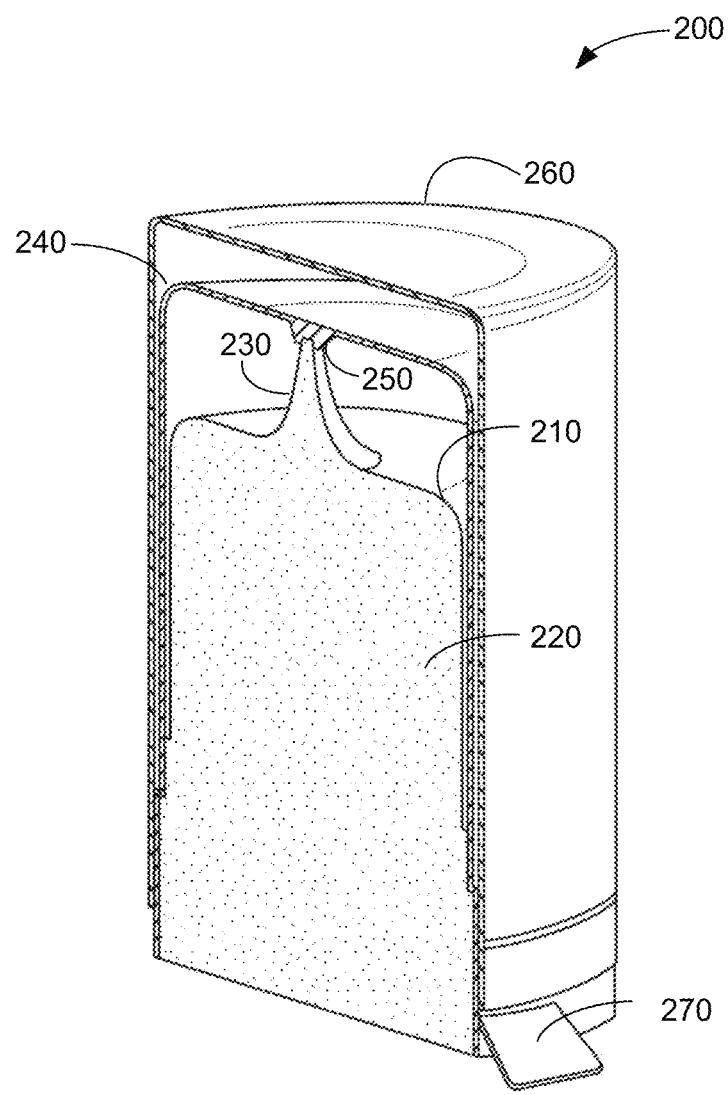

Turning now to FIGS. 1 and 2, there is illustrated a container-closure system that includes a vented cap and a non-vented cap. For purposes of simplicity, the embodiments illustrated in the figures will be described as container-closures, although it is understood that such embodiments are also applicable to drug delivery systems of various types. The container-closure 100, 200 shown in FIGS. 1 and 2 and other figures may be configured to dispense a preservative-free therapeutic agent. The container-closure system 100, 200 includes a container 110, 210 having an enclosure 120, 220 configured to store a therapeutic liquid therein. The enclosure 120, 220 is sterile in various embodiments where the enclosure 120, 220 is implemented to store a therapeutic liquid. It is noted that the container-closure embodiment depicted in FIGS. 1 and 2 and other figures can also be configured for dispensing therapeutic agents that include a preservative.

The container 110, 210 has a dispensing tip 130, 230 through which the therapeutic liquid is dispensed. The dispensing tip 130, 230 has a generally tapered, conical shape that is appropriately dimensioned for dispensing the therapeutic agent to a localized portion of a user's body, such as the eyes, nostrils, and/or ears. For example, the enclosure 110, 210 can be implemented to contain a preservative-free ophthalmic therapeutic agent and the dispensing tip 130, 230 may be configured to enable a user to dispense the ophthalmic therapeutic agent multiple times to the eyes over an extended period of time, such as one month. The container and the dispensing tip may be formed of low-density polyethylene, high-density polyethylene, and/or high-impact polystyrene.

A variety of therapeutic agents can be dispensed using container-closure systems implemented in accordance with embodiments of the disclosure. A non-limiting, non-exhaustive list of such therapeutic agents includes bimatoprost, brimonidine, timolol, cyclosporine, gatifloxacin, ocufloxacin, prednisolone, carnitine and ketorolac. The systems implemented in accordance with embodiments of the disclosure are not limited to delivery of preservative-free therapeutic agents, but can also be applied to delivery of preserved therapeutic agents.

According to some embodiments, the container 110, 210 includes a unidirectional valve, which may optionally include a filter. The unidirectional valve is configured to allow the therapeutic agent contained within the container to pass through to the dispensing tip 130, 230, but prevents re-entry of the therapeutic agent and/or other fluids or contaminants into the container. Various types of valves can be implemented to provide unidirectional flow of fluid from the container to the dispensing tip 130, 230, including the Novelia valve available from Rexam and the valve system of the Ophthalmic Squeeze Dispenser available from Aptar Pharma, for example.

In some embodiments, the container 110, 210 is configured to dispense a single dose of the therapeutic agent on a repeated basis over a predetermined duration of time. For example, the container 110, 210 can be configured to dispense single doses of the therapeutic agent each day for a month. According to some embodiments, the container 110, 210 is configured to dispense a predetermined volume of the therapeutic agent as a single dose. In such embodiments, the unidirectional valve can be configured to regulate the volume of the therapeutic agent so that a metered dose of the therapeutic agent is dispensed during each application. Suitable precision metering valves are available from Rexam, for example. Also, various available spring-loaded unidirectional valves can be used that open during actuation to deliver a single dose of drug product. After actuation, the valve returns to its original position and seals the opening. According to various embodiments, the container-closure system described herein can be implemented with a squeezable vessel. Alternatively, or in addition, a pump mechanism can be implemented to facilitate metered or unmetered dispensing of a therapeutic agent contained within the container 110, 210.

A vented cap 140, 240 that includes one or more vents 145 is fitted over at least a portion of the container 110, 210 allowing passage of ambient air between the vented cap 140, 240 and the dispensing tip 130, 230. The one or more vents 145 may be configured to allow passage of air into and out of a cavity between the dispensing tip 130, 230 and the vented cap 140, 240 sufficient to accelerate drying of residual therapeutic liquid and/or other contaminants at the dispensing tip 130, 230 of the container 110, 210 after dispensing the therapeutic liquid dose.

The container-closure system 100, 200 shown in FIGS. 1 and 2 and other figures includes a protrusion 150, 250 which is configured to releasably engage a distal portion of the dispensing tip 130, 230. When properly positioned at the distal portion of the dispensing tip 130, 230, a seal is formed between the vented cap 140, 240 and the dispensing tip 130, 230. Depending on the nature of the therapeutic agent and the application of use, the seal can be implemented to provide a desired degree of sealing (e.g., fluid-tight, air-tight, or mechanically tight).

An over cap 160 is fitted over at least a portion of the vented cap 140. The over cap 160 covers the one or more vents 145 to help maintain sterility during storage of the container 110. In some cases, the over cap 160 and the vented cap 140 define an integral structure. According to various implementations described herein, the over cap 160 is configured to be removed from the vented cap 140.

According to some embodiments, antimicrobial additives are provided at selected surfaces of the container-closure system, such as on surfaces of a dispensing tip, the vented cap, and/or the over cap which are susceptible to microbial contamination. A variety of ophthalmic multi-dose container-closure systems and drug delivery systems can benefit from inclusion of antimicrobial surface protection according to embodiments of the disclosure, including those that contain unpreserved, partially preserved, and preserved ophthalmic products.

For example, the following antimicrobial additives can be incorporated in a coating that can be applied to polymeric material suitable for fabricating container-closure systems according to other embodiments of the disclosure: silver nanoparticles, biosafe, IRGAGUARD® F3000, Triclosan, zinc omadine, zinc ion, cupper ion, cerium ion, GOLD-SHIELD®, AEGIS™ antimicrobial, PEI-TCS polymers, protamine sulfate and chlorhexidine, alone or in any combination thereof.

One or more of the vented cap, the over cap, and the dispensing tip may include a desiccant system to promote accelerated drying of residual therapeutic liquid and/or other contaminants. A non-limiting, non-exhaustive list of such therapeutic agents includes silica gel, calcium oxide, and molecular sieve.

A tamper evident seal 170, 270 is fitted over a portion of the over cap 160, 260. In some cases in FIGS. 1, 2, and other figures, the tamper evident seal 170, 270 is a band that wraps around a portion of the container 110, 210 and/or the over cap 160, 260. In some cases, the tamper evident seal 170, 270 covers all of or substantially all of the container 110, 210 and/or the over cap 160, 260. The tamper evident seal 170, 270 is configured to break when a force is applied by a user. In the representative examples shown in FIGS. 1 and 2, the tamper-evident seal 170, 270 is attached to the over cap 160, 260, and breaking the tamper-evident seal 170, 270 causes the over cap 160, 260 to be removed from the container 110, 210. In some cases, the over cap 160, 260 is configured to be discarded when the tamper-evident seal 170, 270 is removed, leaving the vented cap 140, 240 on the container 110, 210.

Figure 3:
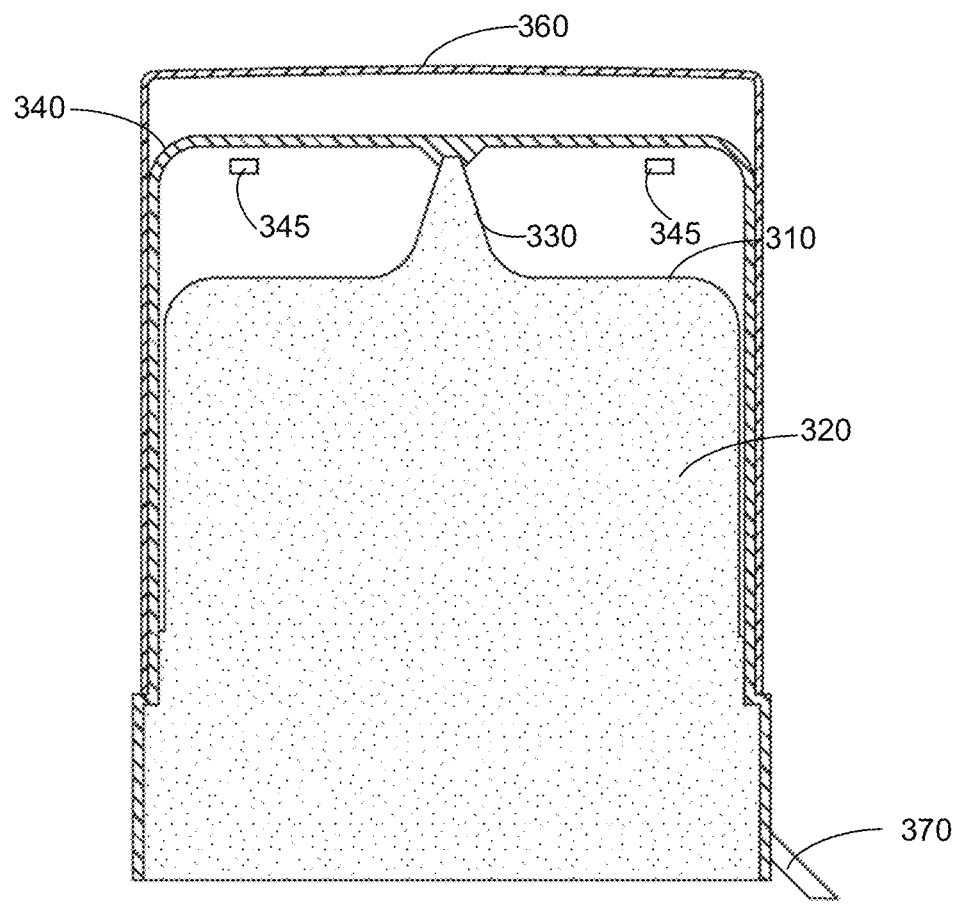
FIGS. 3 and 4 illustrate a container-closure system that includes a vented cap, an over cap, and a tamper evident seal configured to be broken causing the tamper-evident seal to be removed from the container without removing the over cap.
Figure 4:
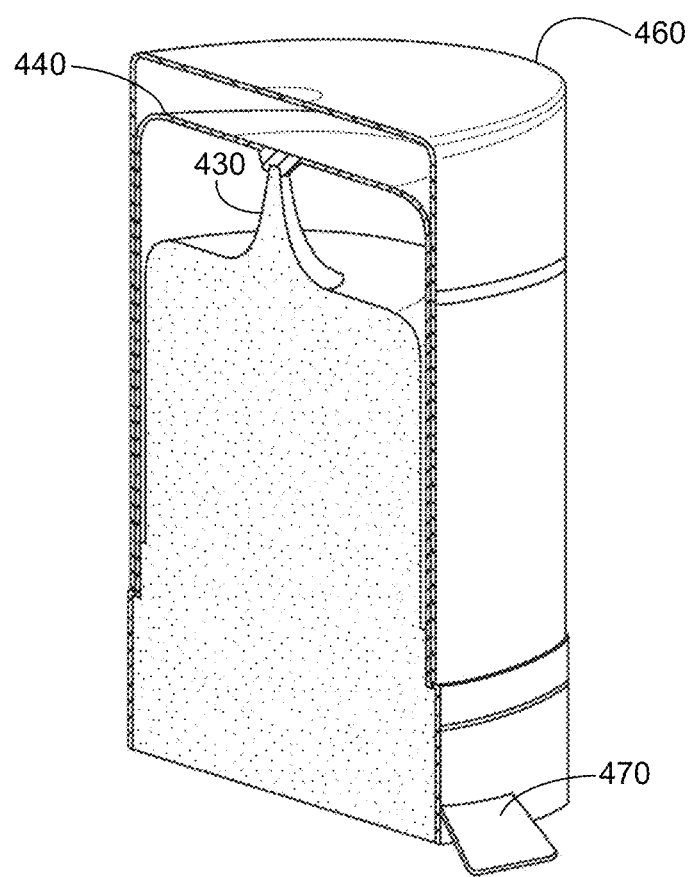

In some cases, breaking of the tamper evident seal does not remove the over cap from container-closure system. In the representative examples illustrated in FIGS. 3 and 4, the tamper-evident seal 370, 470 is configured to be broken and removed without removing the over cap 360, 460. In some embodiments, the over cap 360, 460 and the vented cap 340, 440 define an integral structure, such that when using the container to apply the therapeutic liquid, the vented cap 340, 440 and the over cap 360, 460 are removed together to provide access to the dispensing tip 330, 430 and replaced after application of a dose of the therapeutic liquid. In some implementations, the tearing of the tamper evident seal 370, 470 exposes the vents 345 in the vented cap and/or the over cap. According to various embodiments, the over cap 360, 460 is configured to be removed so as to expose the one or more vents 345 on the vented cap 340, 440, and the vented cap 340, 440 is configured to be removed to expose the dispensing tip 330, 430.

Figure 5:
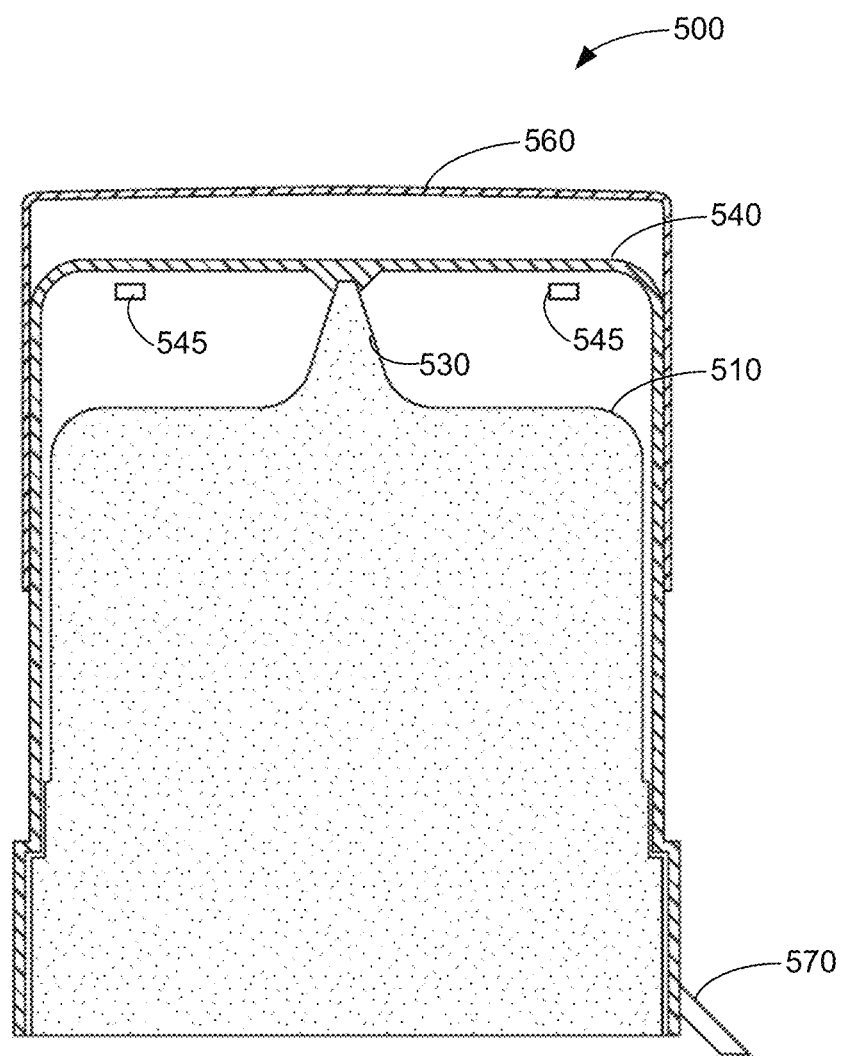
FIGS. 5-7 show container-closure systems in which the over cap includes one or more vents and is configured to be rotated with respect to the vented cap and the container, such that at least one vent disposed on the over cap and at least one vent disposed on the vented cap can overlap.
Figure 6:
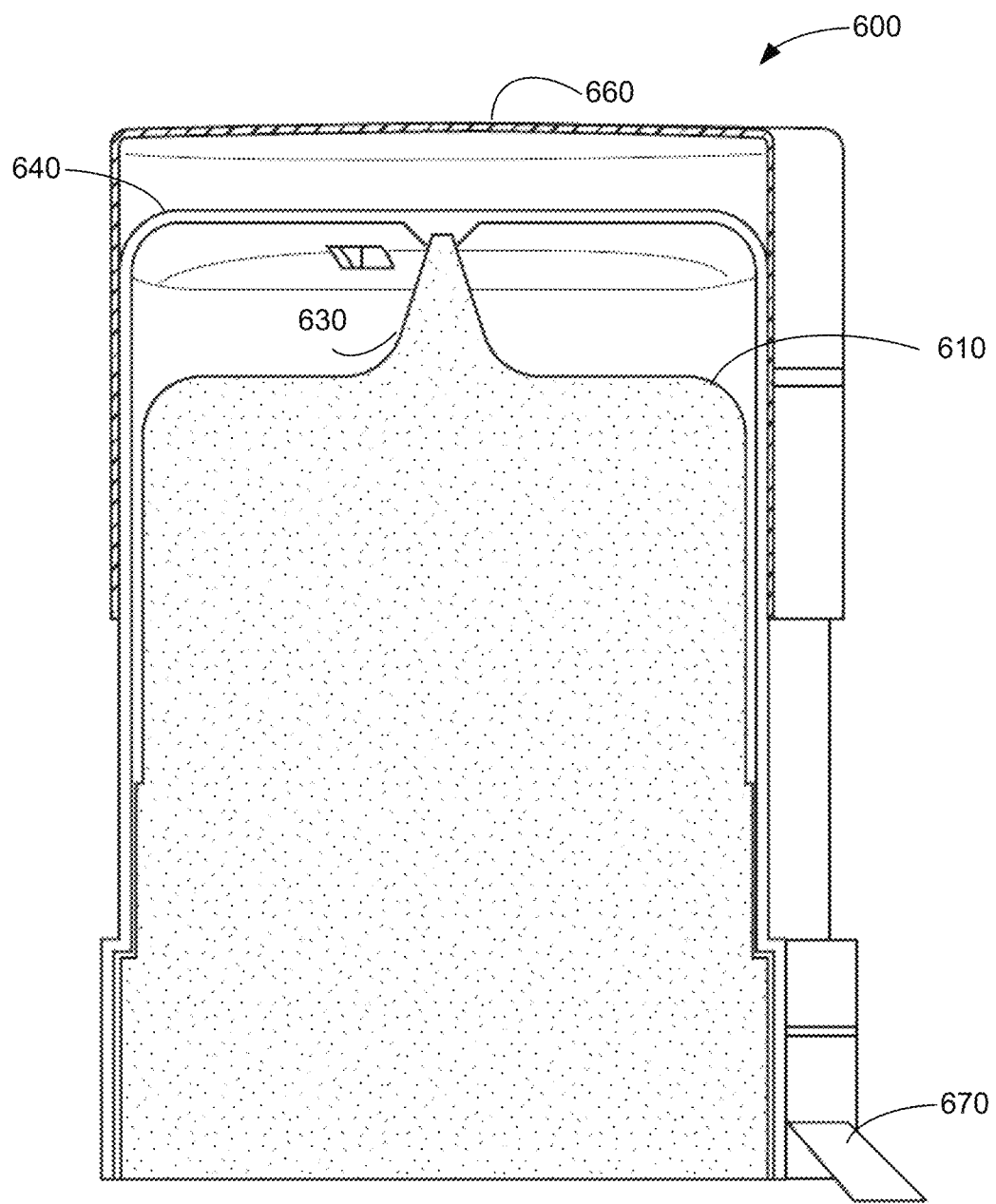
Figure 7:
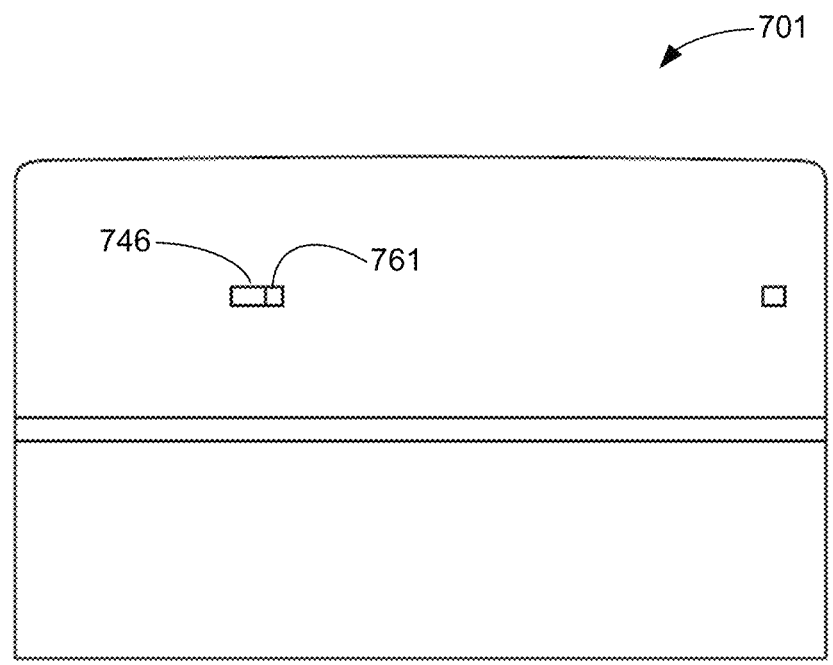

According to various aspects described herein, the over cap includes one or more vents. FIGS. 5-7 illustrate a representative example in which the over cap 560, 660 includes one or more vents and is configured to be rotated with respect to the vented cap 540, 640 and the container 510, 610, such that at least one vent disposed on the over cap and at least one vent disposed on the vented cap 540, 640 overlap causing the dispensing tip 530, 630 to be exposed to the ambient air through the overlapping vents. In this representative example, the vented cap 540, 640 and the over cap 560, 660 may define an integral structure or may be separate removable structures as described previously. A tamper evident seal 570, 670 is attached to at least one of the over cap 560, 660, and the vented cap 540, 640. The tamper evident seal 570, 670 is configured to be broken off from the over cap 560, 660 and/or the vented cap 540, 640.

FIG. 5 shows a container-closure system 500 comprising a vented cap 540 that includes one or more vents 545 and an over cap 560 disposed over at least a portion of the vented cap 540. In this representative example, the over cap 560 prevents the one or more vents 545 on the vented cap 540 from allowing ambient air into the cavity between the vented cap 540 and the dispensing tip 530. FIG. 6 illustrates the same container-closure system 500, 600 as FIG. 5, but with the over cap 660 rotated with respect to the vented cap 640. Vents on the over cap 660 at least partially overlap with vents on the vented cap 640, causing the dispensing tip 630 to be exposed to ambient air through the overlapped vents.

FIG. 7 illustrates a cap assembly 701 comprising an over cap and a vented cap. As described previously, in connection with FIGS. 5 and 6, this representative example includes a vented over cap. FIG. 7 shows vents on the over cap partially overlapping with vents on the vented cap, allowing passage of air through the vents. A portion of the vent 746 is covered by a portion 761 of the over cap.

The foregoing description of the representative embodiments has been presented for the purposes of illustration and description. It is not intended to be exhaustive or to limit the invention to the precise form disclosed. Many modifications and variations are possible in light of the above teaching. Any or all features of the disclosed embodiments can be applied individually or in any combination are not meant to be limiting, but purely illustrative. It is intended that the scope of the invention be limited not with this detailed description, but rather determined by the claims appended hereto.

What is claimed is:

1. An apparatus for dispensing a sterile, non-preserved therapeutic liquid, comprising:
    a container configured to hold the sterile, non-preserved therapeutic liquid and having a dispensing tip configured to dispense a dose of the therapeutic liquid;
    a vented cap configured to fit over at least a portion of the container including the dispensing tip and having one or more vents that allow air to pass into and out of a cavity defined between the vented cap and the dispensing tip;
    a second cap configured to fit over at least a portion of the vented cap; and
    a tamper evident seal coupled to the second cap and one or both of the container and the vented cap.

2. The apparatus according to claim 1, wherein the container is configured to dispense a plurality of single doses of the therapeutic liquid in the form of an ophthalmic solution, emulsion or suspension.

3. The apparatus of claim 1, wherein one or more vents in the vented cap are configured to allow passage of air into and out of the cavity sufficient to accelerate drying of residual therapeutic liquid at the dispensing tip of the container after dispensing the therapeutic liquid dose.

4. The apparatus of claim 1, wherein the second cap is configured to be twisted and removed from the apparatus, and the tamper evident seal is configured to break in response to the twisting of the second cap.

5. The apparatus of claim 1, wherein the vented cap and the second cap define an integral structure, and the tamper evident seal is configured to break away from the second cap.

6. The apparatus of claim 1, wherein the vented cap, the second cap, and the tamper evident seal define an integral structure, and the tamper evident seal is configured to break away from the vented cap and the second cap.

7. The apparatus of claim 6, wherein the second cap defines a second vented cap, and twisting the second vented cap relative to the container causes vents of the vented cap and the second vented cap to overlap.

8. The apparatus of claim 7, wherein the container contains more than one dose of the therapeutic liquid.

9. The apparatus of claim 1, wherein the vented cap comprises a protrusion arranged on the vented cap to establish contact with the dispensing tip of the container when the vented cap is fitted on the container.

10. The apparatus of claim 9, wherein the protrusion is configured to seal the dispensing tip of the container when the vented cap is fitted on the container.

11. The apparatus of claim 1, wherein the second cap comprises a desiccant system.

12. The apparatus of claim 1, wherein one or both of the dispensing tip of the container and the vented cap comprise an antimicrobial.

13. The apparatus of claim 1, wherein the vented cap and the dispensing tip are connected.

14. The apparatus of claim 1, wherein the therapeutic liquid is in solution, emulsion or suspension form, and has a therapeutic agent selected from the group consisting of bimatoprost, brimonidine, timolol, cyclosporine, gatifloxacin, ocufloxacin, prednisolone, carnitine and ketorolac.

15. The apparatus of claim 14, wherein the container comprises a unidirectional valve situated at the dispensing tip and configured to prevent fluid return to the container.

16. The apparatus of claim 15, wherein the uni-directional valve is configured to prevent contamination of the therapeutic liquid from a source external to the container.

17. The apparatus according to claim 1, wherein the container and the dispensing tip are formed of one or more polymers selected from the group consisting of low-density polyethylene, high-density polyethylene, and high-impact polystyrene.

18. A method, comprising:
   storing a sterile, non-preserved therapeutic liquid in a reservoir of a container configured to hold the sterile, non-preserved therapeutic liquid, the container comprising:
   a dispensing tip configured to dispense a dose of the therapeutic liquid;
   a vented cap configured to fit over at least a portion of the container including the dispensing tip and having one or more vents that allow air to pass into and out of a cavity defined between the vented cap and the dispensing tip;
   a second cap configured to fit over at least a portion of the vented cap; and
   a tamper evident seal coupled to the second cap and one or both of the container and the vented cap.

19. The apparatus according to claim 18, wherein the container is configured to dispense a plurality of single doses of the therapeutic liquid in the form of an ophthalmic solution, emulsion or suspension.

20. A method, comprising:
   removing a cap from a container configured to hold a non-preserved, sterile therapeutic liquid, the container comprising a dispensing tip configured to dispense a dose of the non-preserved, sterile therapeutic liquid, the cap comprising:
   a vented cap configured to fit over at least a portion of the container including the dispensing tip and having one or more vents that allow air to pass into and out of a cavity defined between the vented cap and the dispensing tip;
   a second cap configured to fit over at least a portion of the vented cap; and
   dispensing the therapeutic liquid from the container.

* * * * *